United States Patent [19]

Mora

[11] Patent Number: 4,495,186
[45] Date of Patent: Jan. 22, 1985

[54] ORGANOMETAL COMPLEXES OF N-CYCLOHEXYL-PIPERAZINO ACETAMIDES OR PROPIONAMIDES, PREPARATION AND USE THEREOF AS ANTIULCER-ANTISECRETIVE-BUFFERING DRUGS

[75] Inventor: Camillo C. Mora, Piacenza, Italy
[73] Assignee: Camillo Corvi S.p.A., Italy
[21] Appl. No.: 462,138
[22] Filed: Jan. 31, 1983
[30] Foreign Application Priority Data
   Apr. 5, 1982 [IT] Italy ............................... 20583 A/82
[51] Int. Cl.$^3$ .................... A61K 31/495; C07D 295/02
[52] U.S. Cl. .................................... 514/255; 544/225; 544/400; 536/121
[58] Field of Search ................ 544/400, 225; 424/245, 424/250; 260/448 AD, 446; 536/121

[56] References Cited

U.S. PATENT DOCUMENTS 2,910,493 10/1959 Rinse et al. .................. 260/448 AD
3,629,229 12/1971 Schmank ............................ 536/121
3,880,901 4/1975 Turner ......................... 260/448 AD
4,278,796 7/1981 Corvi-Mora ........................ 544/400

FOREIGN PATENT DOCUMENTS 394162 3/1974 Spain .

OTHER PUBLICATIONS

Di Nola, R. et al., Chem Abstract, vol. 83, 1975, p. 27, 157844q.
Laboratorios Robert S.A., Chem. Abstract, vol. 83, 1975, p. 291, 197799k (Span 3941 62).
R. Di Nola, Gaz. Med. It., 134, 1975, pp. 95–102.

Primary Examiner—Paul M. Coughlan, Jr.
Assistant Examiner—Cecilia Shen
Attorney, Agent, or Firm—Ostrolenk, Faber, Gerb & Soffen

[57] ABSTRACT

The invention relates to complex salts of N-cyclohexyl-piperazino-acetamides or propionamides with dihydroxy aluminum-α-hydroxy-carboxylates, a process for preparing them and the use thereof as antiulcer-antisecretive-buffering drugs.

7 Claims, No Drawings

ORGANOMETAL COMPLEXES OF N-CYCLOHEXYL-PIPERAZINO ACETAMIDES OR PROPIONAMIDES, PREPARATION AND USE THEREOF AS ANTIULCER-ANTISECRETIVE-BUFFERING DRUGS

DESCRIPTION OF THE INVENTION

The present invention relates to complex salts having pharmacological activity. More particularly, this invention concerns complex salts, the cation of which is constituted by a cyclohexyl-piperazino-acetamide or propionamide and the organometal anion of which is formed by a dihydroxy aluminum-α- hydroxycarboxylate. Said complex salts perform contemporaneously antiucler, antisecretive as well as buffering activity.

U.S. Pat. No. 4,123,530, of the same Applicant, describes novel derivatives of piperazino and homologues thereof of the formula:

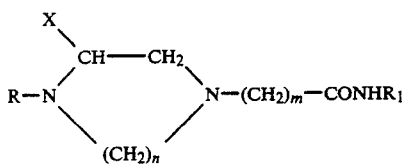

(II)

wherein R is hydrogen, a $C_1$-$C_6$ alkyl group, or a $C_1$-$C_3$ hydroxyalkyl group, $R_1$ is one of the following groups: cycloalkyl, optionally substituted, phenyl, optionally substituted, norbornyl, bornyl, or cinnamyl, X is hydrogen or methyl n is 2 or 3 and m is 1, 2 or 3.

Two of said formula (II) compounds, have shown to be particularly useful from the pharmacologic point of view, since they perform a considerable antisecretive and antiulcer activity. They are N-cyclohexyl-1-piperaziniylacetamide and N-4-methyl-cyclohexyl-1-piperazinylacetamide.

However, the compounds of the above mentioned U.S. Patent cannot be applied in all the pharmaceutic forms because of their high basicity.

Also the inorganic acid salts and organic acid salts which are usually employed in the pharmaceutical industry cannot be applied in all the pharmaceutic forms, with the exception of the monohydrochloride which, however, presents remarkable preparation problems, since among other things, a N-cyclohexyl piperazinyl acetamide base free from disubstituted product must be used.

Organometal anions as derived by combining aluminum hydroxide with α-hydroxy-carboxylic acids are already known from the technical literature. Generally, they are combined by salification with tris-(hydroxymethyl)-aminomethane (THAM, also named TRIS buffer). TRIS buffer is an organic base endowed with buffering power, which, however, does not posses any pharmacologic property of systemic character.

It has now been found that by salifying the N-cyclohexyl-piperazino acetamide bases with a dihydroxy aluminum α-hydroxy carboxylate, deriving preferably from lactic, tartaric orglucoleptonic acid and more preferably from gluconic acid, complex salts are obtained which accomplish contemporaneously an antiulcer and antisecretive activity as well as an excellent buffering action.

These novel complex salts are fully water soluble.

According to this invention, in addition to the N-cyclohexyl-piperazino-acetamide bases, other cations of formula (II) may be used, among which N-4'-methyl-cyclohexyl-1-piperazino-acetamide is particularly mentioned.

Dihydroxy-aluminate-gluconate of N- cyclohexyl-1-piperazino-acetamide which, at present, constitutes the most preferred compound of the present invention, can be represented by the following structural formula:

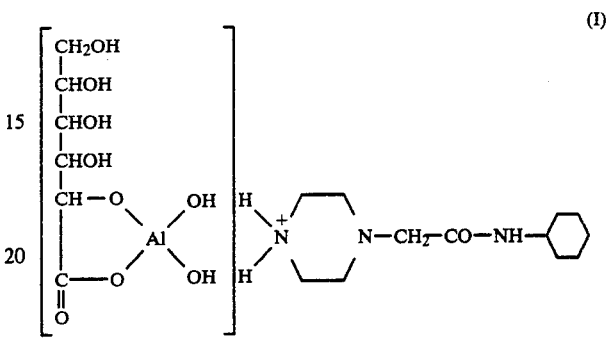

formula: $C_{18}H_{36}$ Al $N_3$ $O_{10}$; M.W.480.461

In the following example, the process of this invention is specified. It occurs continuously without separation of the intermediates, with a substantially quantitative yield. It is not limiting the scope of the present invention.

EXAMPLE 1

Into a 5 liter reactor, provided with a heating mantle, thermometer, reflux condenser with a collecting head for the distillate, and stirrer, 329.5g of a 50% (w/w) aqueous solution of C.P. gluconic acid (M.W. 196.16=0.840 mole) is charged and then, after diluting with 480ml. of water, 175.07 g. of 98% aluminum isopropylate (corresponding to 171.57 g. at 100%) (M.W. 204.25=0.840 mole) is introduced and the mixture is heated 4 hours at 75° C. under stirring, while maintaining a nitrogen stream, to achieve the complete dissolution of the components. During heating, the collection of diluted isopropanol is carried out. When the reaction is completed, the mixture is taken again to the initial volume with water, it is Permitted to cool to room temperature, celite (diatomaceous earth) is added and the resulting mixture is filtered in order to eliminate small suspended particles. A complexometric titration is effected so as to control the titre as well as the yield which results to be substantially quantitative (188.9 g of 100% aluminum gluconate; M.W. 225.131=0.839 mole).

To the so obtained solution, there is added gradually, while controlling by means of a pH-meter, a 10% aqueous solution w/v of very pure N-cyclohexyl-1-piperazino-acetamide: an amount equal to 0.839 mole; i.e. 189.05g at 100%, (M.W.225.3), the pH being adjusted to 8.35–8.36. A complete solution is obtained, which is dried using a spray-drier.

The dry product has a titre of 98.5–99% with a yield of 97–98%.

Identification of the obtained product.

| Elemental analysis | | | | |
|---|---|---|---|---|
| Calculated for: | C % = | 44.90 | Found: C % = | 44.45% |
| | H % = | 7.54 | H % = | 7.42% |

-continued

| Elemental analysis | | | |
|---|---|---|---|
| Al % = | 5.60 | Al % = | 5.49% |
| N % = | 8.73 | N % = | 8.64% |
| O % = | 33.23 | | |
| | 100.000 | | |

NMR $^{13}$C, internal reference dioxane, deuterated water solvent, spectrum totally decoupled from hydrogen, signals expressed as δ p.p.m. from tetramethylsilane (T.M.S.) Equipment: Varian XL 100 183 (COO); 170 (CONH); 77.2 (CHOH at α to the carbonyl); 74.6 (CHOH at β to the carbonyl); 70.8 and 69.6 (2 e,uns/C/HOH at γ and δ to the carbonyl); 62.8 (CH$_2$OH); 60.3 (COCH$_2$N); 31.9, 25.0 and 24.5 (CH$_2$ of the cyclohexane ring).

Buffering effect: to 4.6 g of the sample, in a 1000 ml beaker, 400 ml of 0.015 N HCl are added, while keeping the temperature at 37° C. (thermostat). The pH is measured after 30 minutes, while controlling that it be maintained within 4.8÷5.0. Then, by means of a burette, 0.1 N HCl is introduced at a rate of 1 ml/minute, to achieve a pH of 3.0. 165 ml of 0.1N HCl must be consumed at the very least.

Pharmaco-toxicologic results

The acute toxicity of the complex salt of dihydroxy-aluminum-gluconate of N-cyclohexyl-piperazino acetamide is checked by the usual pharmacotoxicologic testing on the rat and mouse per os, the results of which are given in the following table.

TABLE 1

| Animals | Administration route | LD$_{50}$ mg/kg | Fiduciary limits |
|---|---|---|---|
| Rat | os | 6668.4 | (8447.4–5264.6) |
| Mouse | os | 6241.9 | (6646.4–5862.2) |

The toxicity is very low, even in relation to the high therapeutical dosage which is required in this case.

Concerning the pharmacological activity, the complex salt of the present invention shows a neutralizing action for gastric hyperacidity, accompanied by an antisercretive and antiulcer action, which are proved by the ED$_{50}$ values on the rat, as referred to below:

Buffering activity

Rat ED$_{50}$ = 156 mg/kg os.

Antisecretive activity

Rat ED$_{50}$ = 330 mg/kg os.

The antiulcer activity has been tested on the rat for different types of experimental ulcer. The obtained therefrom is in Table 2.

TABLE 2

| Animal | Type of experimental ulcer | Administration | ED$_{50}$ mg/kg |
|---|---|---|---|
| Rat | Phenylbutazone + hystamine | os | 150 |
| Rat | Reserpine | os | 480 |
| Rat | Immobilization | os | 420 |
| Rat | Fast | os | 350 |
| Rat | Shay | i.d. | 360 |
| Rat | Duodenal from cystamine | i.d. | 270 |
| Rat | From indomethacin | os | 420 |

The complex salts of this invention can advantageously be used as oral pharmaceutic forms, characterized by a strong dispersion capability, particularly masticable tablets with a high disintegrability degree, and suspensions, in inert pharmaceutically acceptable vehicles, of granulates or microencapsulated powders.

In the case of the above referred specific forms, in which the disperse state is to aid contact with the mucous membrane in which the pH increase is to be effected, the complex salt can be admixed with the usual pharmaceutically acceptable auxiliary agents, as well as aromatisers and sweeteners.

The drug obtained according to the present invention is useful for the therapy of all forms of gastric hyperacidity as in gastroduodenal ulcers, as well as for the treatment of pyrosis, gastralgia and gastritis.

A suggested posology is 400 mg 2–3 times daily, to a total of 800–1200 mg/pro die.

I claim:

1. Salt of N-cyclohexyl-piperazino-acetamide or propionamide with dihydroxy aluminum-α-hydroxy-carboxylate.

2. A salt according to claim 1, consisting essentially of dihydroxy aluminum gluconate of N-cyclohexyl-piperazino-acetamide, having the formula

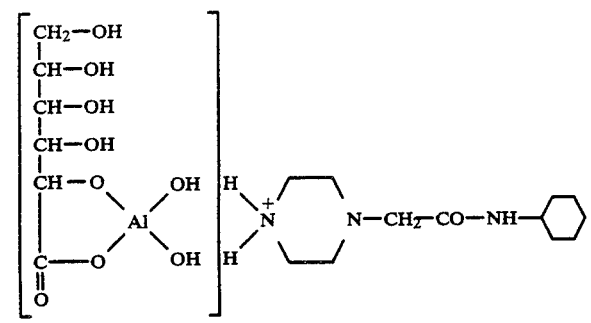

3. A process for preparing the salt consisting essentially of dihydroxy aluminum gluconate of N-cyclohexyl piperazino acetamide, characterized in that it is carried out without intermediate isolation, starting from a 50% aqueous solution of gluconic acid, reacting it with a stoichiometric amount of aluminum isopropylate, heating, under a nitrogen stream, to completion of the reaction for forming the dihydroxy-aluminum gluconate anion, and, after eliminating the isopropyl alcohol, diluting with water of the filtered mass, the actual stoichiometric amount as determined by titration, salifying with an equivalent aqueous solution of N-cyclohexyl-piperazino-acetamide, and dessicating the so obtained salt by evaporation.

4. A process according to claim 3, characterized in that the solution of N-cyclohexyl-piperazino-acetamide is free from disubstituted product.

5. A pharmaceutical preparation with antiulcer, antisecretive and buffering action, which contains a salt according to claim 1, together with one or more vehicles and/or pharmacologically inert and non-toxic excipients 6. A pharmaceutical preparation with antiulcer, antisecretive and buffering action in a unit dose containing 400 mg of a salt according to claim 2.

7. A salt according to claim 1 consisting essentially of dihydroxy aluminum gluconate of N-4'-methyl-cyclohexyl-1-piperazino-acetamide.

* * * * *